United States Patent [19]

Timmins et al.

[11] Patent Number: 4,883,792

[45] Date of Patent: Nov. 28, 1989

[54] STEROID CREAM FORMULATION

[76] Inventors: Peter Timmins, 6 Copse Grove, Irby, Wirral, Merseyside, L61 4YP; Nicholas I. Payne, 50 Romsey Avenue, Fareham, Hants, PO16 9TA, both of United Kingdom

[21] Appl. No.: 297,159

[22] Filed: Jan. 17, 1989

[51] Int. Cl.$^4$ .................. A61K 9/06; A61K 31/58
[52] U.S. Cl. ................... 514/169; 514/179; 514/252; 514/399
[58] Field of Search ............... 514/169, 179, 252, 399

[56] References Cited

U.S. PATENT DOCUMENTS

| | | | |
|---|---|---|---|
| 3,892,857 | 7/1975 | DiFazio et al. | 424/241 |
| 4,247,552 | 1/1981 | Hallesy et al. | 514/252 |
| 4,277,475 | 7/1981 | Vickery | 514/399 |
| 4,361,559 | 11/1982 | Varma et al. | 424/243 |
| 4,439,441 | 3/1984 | Hallesy et al. | 514/399 |
| 4,446,145 | 5/1984 | Van Bever | 514/399 |
| 4,636,520 | 1/1987 | Umio et al. | 514/399 |
| 4,661,493 | 4/1987 | Gibbs | 514/252 |
| 4,782,059 | 11/1988 | Gade Busch et al. | 514/252 |
| 4,868,169 | 9/1989 | O'Laughlin et al. | 514/179 |

FOREIGN PATENT DOCUMENTS 316834 5/1989 European Pat. Off. .

OTHER PUBLICATIONS

Devlin et al., C.A. 104:162132n, (1986).
Nagova et al., C.A. 103:200777r, (1985).
Varma et al., C.A. 98:143772w, (1982), of U.S. Pat. No. 4,361,559, Nov. 30, 1982.
Wojnar et al., 106:78900v, (1986).
Lutsky et al., C.A. 106:78939q, (1985).
Lan et al., C.A. 110:108385h, (1988).

*Primary Examiner*—Shep K. Rose
*Attorney, Agent, or Firm*—Burton Rodney

[57] ABSTRACT

A steroid cream formulation which has enhanced physical and chemical stability is formed of $(11\beta,17\alpha)$-17-(ethylthio)-9$\alpha$-fluoro-11$\beta$-hydroxy-17-(methylthio)androsta-1,4-dien-3-one (tipredane), and a vehicle containing as major ingredients propylene glycol and water together with a sodium citrate or potassium citrate buffer to impart an acid value to the cream formulation of greater than 3, a high melting point wax, such as white wax, to impart proper consistency without adversely affecting stability of the tipredane, benzyl alcohol as a preservative, together with one or more emulsifiers, which include glyceryl stearate, one or more emollients which include isopropyl isostearate or isopropyl palmitate, lubricants and other conventional cream formulation ingredients.

20 Claims, No Drawings

STEROID CREAM FORMULATION

FIELD OF THE INVENTION

The present invention relates to a steroid cream formulation which has enhanced physical and chemical stability and contains (11β, 17α)-17-(ethylthio)-9α-fluoro-11B-hydroxy-17-(methylthio)androsta-1,4-dien-3-one (tipredane) as an active ingredient.

BACKGROUND OF THE INVENTION

U.S. Pat. No. 4,361,559 to Varma discloses antiinflammatory 17,17-bis(substituted thio)androstenes of the formula

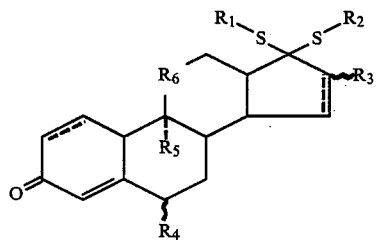

wherein
$R_1$ and $R_2$ are the same or different and each is alkyl, cycloalkyl or aryl;
$R_3$ is hydrogen, hydroxy, alkoxy, aryloxy, alkylthio, arylthio,

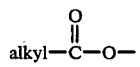

or halogen;
$R_4$ is hydrogen, methyl, hydroxy,

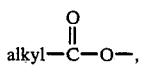

or halogen;
$R_5$ is hydrogen or halogen; and
$R_6$ is carbonyl or B-hydroxymethylene. A broken line in the 1,2-,6,7- and 15,16-position of a structural formula indicates the optional presence of ethylenic unsaturation.

Includes among the compounds covered in the Varma patent is tipredane which has been found to be a highly effective topical antiinflammatory agent.

Tipredane is practically insoluble in water (less than 0.0002 mg/ml at 25° C.); 1:1 hydroalcoholic mixtures of tipredane are stable at pH 6.5-8.0 and unstable under acidic conditions while tipredane itself is susceptible to oxidation.

It is known to use monoglycerides such as glyceryl monostearate as a thickener in steroid cream formulations. For example, U.S. Patent No. 3,892,857 to DiFazio et al discloses a cream formulation containing propylene glycol, water and a steroid, namely, 21-chloro-9α-fluoro-Δ⁴-pregnene-11β, 16α, 17α-triol-3,20-dione 16,17-acetonide (halcinonide) and as an oleaginous thickener monoglycerides such as glyceryl monostearate, glyceryl monooleate, glyceryl monopalmitate and glyceryl ricinoleate.

Where it has been attempted to employ generally commercially available glyceryl monostearate in an oil-in-water tipredane cream formulation, it has been found that syneresis of the aqueous phase occurs with some lots of glycyl monostearate.

U.S. application Ser. No. 120,278, filed Nov. 13, 1987, assigned to E. R. Squibb & Sons, Inc., which will issue as U.S. Pat. No. 4,868,169 on Sept. 9, 1989, discloses a tipredane cream formulation which includes tipredane, water, an emulsifier which includes glyceryl monostearate, a buffer, a non-acid long chain fatty acid wax, optionally one or more emollients, optionally one or more chelating agents, optionally one or more lubricants, optionally one or more antioxidants, and optionally one or more skin conditioners.

DESCRIPTION OF THE INVENTION

In accordance with the present invention, a soft, non-greasy, cosmetically elegant topical oil-in-water steroid cream formulation is provided which contains the steroid tipredane as its active ingredient alone or in combination with an antifungal agent and has excellent physical and chemical stability and does not undergo any significant syneresis or bleeding although it contains glyceryl monostearate from any source including commercially available sources heretofore known to cause synerises in tipredane creams. The oil-in-water cream formulation according to the present invention contains in addition to tipredane alone or in combination with an antifungal agent, a carrier vehicle which is formed of one or more solubilizers for the tipredane, water, one or more emulsifiers including glyceryl monostearate, one or more buffers, isopropyl isostearate and/or isopropyl palmitate as an emollient, benzyl alcohol and/or other preservative, optionally one or more other emollients, optionally one or more metal chelating agents, optionally one or more skin conditioners, and optionally one or more silicone lubricants or defoaming agents.

In addition, in order to obtain acceptable consistency and chemical stability, the cream formulation of the invention will include a high melting point wax having a melting point above about 60° C. such as white wax (also referred to as beeswax). It has been found that such wax will impart the desired heat storage stability to the cream but will not interfere with the stability of the tipredane. In addition or in place of white wax, the cream formulation may also include a synthetic beeswax (for example Synchrowax), microcrystalline wax, carnauba wax and the like.

The tipredane steroid will be employed in the form of a micronized powder having an average particle size of within the range of from about 2 to about 10 microns and will be present in an amount within the range of from about 0.005 to about 0.5% by weight and preferably from about 0.05 to about 0.3% by weight based on the total weight of the tipredane cream formulation.

As indicated, the carrier vehicle will contain one or more solubilizers for the tipredane such as propylene glycol which also serves as a preservative, propylene carbonate, polyethylene glycols or dimethylisosorbide or mixtures thereof.

The propylene glycol and/or other solubilizers will be present in an amount within the range of from about 5 to about 30% by weight and preferably from about 10 to about 20% by weight of the cream formulation.

Water which also serves as a solubilizer for a portion of the tipredane will be present in an amount within the range of from about 30 to about 65% and preferably from about 40 to about 60% by weight of the total cream formulation.

An important feature of the cream formulation of the invention is its excellent chemical stability and physical stability so that syneresis or bleeding will not occur even if glyceryl monostearate is present.

The cream formulation will include a thickener, a high melting point wax (melting point above about 60° C.) which is a white wax and/or other wax such as microcrystalline wax, synthetic beeswax, carnauba wax and the like, in an amount within the range of from about 1 to about 10 weight % and preferably from about 2 to about 5 weight % based on the weight of total tipredane cream formulation.

The emulsifier will be present in an amount within the range of from about 5 to about 25 weight % and preferably from about 8 to about 20 weight % based on the weight of the total tipredane cream formulation. Examples of emulsifiers suitable for use herein include but are not limited to glyceryl monostearate, cetyl alcohol, polyethylene glycol 60 sorbitan monolaurate (polysorbate 60), wool alcohols, polyethylene glycol 300 stearate and the like. It is preferred to employ a mixture of such emulsifiers, namely, glyceryl monostearate in an amount of within the range of from about 4 to about 12% by weight and preferably from about 5 to about 9% by weight, cetyl alcohol in an amount within the range of from about 2 to about 10% by weight and preferably from about 4 to about 6% by weight, and polysorbate 60 in an amount within the range of from about 2 to about 8% by weight, and preferably from about 3 to about 6% by weight, all of such % being based on the total weight of the tipredane cream formulation.

The emollients may be present in an amount within the range of from about 0.1 to about 10% and preferably from about 1 to about 5% by weight based on the total tipredane cream formulation. Examples of emollients suitable for use herein include but are not limited to a isopropyl isostearate, isopropyl palmitate, isopropyl myristate, ethylhexyl palmitate and the like.

The cream formulation may optionally include one or more skin conditioners in an amount of within the range of from about 0.1 to about 5% and preferably from about 0.5 to about 3% by weight based on the total tipredane cream formulation, such as an alkoxylated methyl glucose derivative, for example, polypropylene glycol-20 methyl glucose ether (Glucam E-20, trademark of Amerchol Corp, CPC Int.), polypropylene glycol-10 methyl glucose ether (Glucam P-10, trademark of Amerchol Corp, CPC Int.) and polyethylene glycol (10 or 20) ether of methyl glucose. Other skin conditioners that may be employed include allantoin, d- or dl-panthenol, sodium 2-pyrrolidone carboxylic acid and the like.

In addition, the cream formulation will include a silicone lubricant or defoamer in an amount within the range of from about 0.1 to about 2.5% by weight and preferably from about 0.5 to about 1.5% by weight based on the total tipredane cream formulation. Examples of silicone lubricants suitable for use herein include, but are not limited to Dimethicone 350 (Silicone DC 200 Fluid (350 CS)) or Dimethicone 200.

The cream formulation of the invention will include an antioxidant, such as sodium metabisulfite, butylated hydroxytoluene, acetone sodium bisulfite or sodium formaldehyde sulfoxylate in an amount within the range of from about 0.001 to about 0.1% by weight and preferably from about 0.005 to about 0.05% by weight of the tipredane cream formulation. Sodium metabisulfite is preferred.

As the optional metal chelating agent, (or anti-oxidant) disodium or dipotassium ethylene-diamine tetraacetate dihydrate is preferred. Other examples of metal chelating agents which may be employed include citric acid, phosphoric acid or monoisopropyl citrate. The metal chelating will be employed in an amount within the range of from about 0.001 to about 0.01% by weight and preferably from about 0.002 to about 0.008% by weight of the tipredane cream formulation.

In addition to tipredane, the cream formulation of the invention may include an antifungal agent in an amount within the range of from about 1 to about 25% and preferably from about 5 to about 20% by weight of the formulation. Examples of antifungal agents suitable for use herein include, but are not limited to, amphotericin B, nystatin, griseofulvin, miconazole, ketoconazole, tioconazole, econazole, clotrimazole and/or other macrolide antifungal agents.

The following represents preferred oil-in-water cream formulations in accordance with the present invention.

| Ingredient | % by weight | | |
|---|---|---|---|
| Tipredane (in form of micronized powder) | 0.05 | to | 0.3 |
| Antifungal agent (such as tioconazole) | 0 | to | 5 |
| Glyceryl monostearate (emulsifier) | 5 | to | 9 |
| Propylene glycol (solubilizer-preservative) | 10 | to | 20 |
| Sodium citrate monohydrate (buffer) | 0.4 | to | 0.5 |
| Benzyl alcohol (preservative) | 0.8 | to | 1.5 |
| Disodium EDTA dihydrate (metal chelating agent) | 0.002 | to | 0.008 |
| Aluminum hydroxide (buffer) | 0.2 | to | 0.6 |
| White wax (thickener) | 2 | to | 5 |
| Cetyl alcohol (emulsifier) | 4 | to | 6 |
| Isopropyl isostearate (or isopropyl palmitate) | 1 | to | 5 |
| Polysorbate 60 (emulsifer) | 3 | to | 6 |
| Silicone fluid (defoamer) | 0.2 | to | 2 |
| Water | | to | 100%. |

The tipredane cream formulation of the invention may be prepared as described in the working Examples as follows. All components except actives, propylene glycol and benzyl alcohol (if present) are heated and melted at 80 to 85° C. and homogenized for 10 to 30 minutes. The mix is cooled to 50° to 55° C., for example, by air-drying.

The actives, for example, tipredane alone or with, for example, tioconazole, are dissolved in propylene glycol at 50° to 60° C. and the propylene glycol mix is added to the cooled melt described above. While mixing the above mixture, benzyl alcohol (if present) is added and then water is added to bring the mix up to the desired weight. Mixing is continued and the mix is de-aerated under vacuum and cooled to form the cream formulation of the invention.

The following Examples represent preferred embodiments of the present invention. Unless otherwise indicated, all temperatures are expressed in degrees Centigrade.

EXAMPLE 1

A tipredane-tioconazole cream formulation having the following composition was prepared as described below.

| Tipredane-Tioconazole Cream | |
|---|---|
| Ingredient | Amount (mg) |
| Tipredane micronized powder (to supply 1.0 mg/g activity) | 1 |
| Tioconazole | 10 |
| Glyceryl stearate (emulsifier) | 70 |
| Cetyl alcohol NF (emulsifier) | 50 |
| White wax (thickener for proper consistency) | 30 |
| Isopropyl isostearate (emollient) | 33 |
| Tween 60 (polysorbate 60-emulsifier) | 40 |
| Propylene glycol USP (solubilizer-preservative) | 150 |
| Silicone DC200 fluid (350CS) (lubricant-defoamer) | 10 |
| Sodium citrate USP (buffer) | 5 |
| Disodium edetate dihydrate USP (chelating agent-antioxident) | 0.05 |
| Sodium metabisulfite CP (antioxidant) | 0.2 |
| Aluminum hydroxide conc. wet gel (emulsifier-water) | 4 |
| Benzyl alcohol (preservative) | 10 |
| Purified water USP (or equivalent) ca. (sufficient quantity to make 1 g) | 586 |

All components except tipredane, tioconazole, propylene glycol and benzyl alcohol were heated and melted at 80° to 85° C. and homogenized for 20 minutes. The mix was then cooled to 50° to 55° C. by air-drying.

The tipredane with tioconazole were dissolved in the propylene glycol at 50° to 60° C. and the propylene glycol mix was added to the previously formed cooled melt. While mixing the above mixture, benzyl alcohol was added and then water was added to bring the mix up to the desired weight. Mixing was continued and the mix was de-aerated under vacuum and cooled to form the cream formulation of the invention.

The above tipredane-tioconazole cream formulation was found to be a soft cosmetically elegant and non-greasy cream product which had excellent chemical and physical stability and did not undergo syneresis even after prolonged periods of storage at temperatures of 5° C., 25° C. and 40° C.

EXAMPLE 2

A 0.1% w/w tipredane cream formulation having the following composition was prepared employing a procedure similar to that as described in Example 1 except that tioconazole is not employed.

| Tipredane Cream 0.1 W/W | |
|---|---|
| Ingredient | Amount (mg) |
| Tipredane micronized powder (to supply 1.0 mg/g activity) | 1 |
| Glyceryl stearate (emulsifier) | 70 |
| Cetyl alcohol NF (emulsifier) | 50 |
| White wax (thickener for proper consistency) | 30 |
| Isopropyl isostearate | 33 |
| Tween 60 (polysorbate 60-emulsifier) | 40 |
| Propylene glycol USP (solubilizer-preservative) | 150 |
| Silicone DC200 fluid (350CS) (lubricant-defoamer) | 10 |
| Sodium citrate USP (buffer) | 5 |
| Disodium edetate dihydrate USP (chelating agent-antioxident) | 0.05 |
| Sodium metabisulfite CP (antioxidant) | 0.2 |
| Aluminum hydroxide conc. wet gel (emulsifier-water) | 4 |
| Benzyl alcohol (preservative) | 10 |
| Purified water USP (or equivalent) ca. | 595 |

-continued

| Tipredane Cream 0.1 W/W | |
|---|---|
| Ingredient | Amount (mg) |
| (sufficient quantity to make 1 g) | |

The above cream formulation is a soft cosmetic type non-greasy cream product which has excellent physical stability and chemical stability.

EXAMPLE 3

A tipredane cream formulation having the following composition is prepared as described in Example 1 except that isopropyl palmitate is employed in place of isopropyl isostearate.

| Ingredient | mg/g |
|---|---|
| Tipredane | 1 |
| Glyceryl monostearate (wax phase/emulsion stabilizer) | 70 |
| Cetyl alcohol (wax phase) | 50 |
| White wax (also known as beeswax) (wax phase) | 30 |
| Isopropyl palmitate (emollient) | 30 |
| Tween 60 (emulsifier) | 40 |
| Propylene glycol USP (solubilizer, humectant, preservative) | 150 |
| Silicone fluid DC 200 (lubricant, antifoam) | 10 |
| Sodium citrate USP (pH adjuster) | 5 |
| Disodium edetate dihydrate (chelating agent) | 0.05 |
| Sodium metabisulfite (antioxidant) | 0.2 |
| Aluminum hydroxide conc. wet gel (pH adjuster) | 4 |
| Benzyl alcohol (preservative) | 7.5 |
| Purified water to 1.0 g. | |

The above cream formulation is a soft cosmetic type non-greasy cream product which has excellent physical and chemical stability.

What is claimed is:

1. A tipredane and antifungal agent cream formulation having enhanced chemical and physical stability comprising solubilized tipredane, and a vehicle comprising a solubilizer for tipredane, water, at least one emulsifier which includes glyceryl monostearate, at least one buffer, a high melting point wax to impart desired consistency and heat storage stability to the cream formulation, one or more emollients including isopropyl stearate or isopropyl palmitate, and mixtures thereof with one or more metal chelating agents, and mixtures thereof with one or more lubricants, and mixtures thereof with one or more antioxidants or preservatives, and mixtures thereof with one or more antifungal agents, wherein said antifungal agent is amphotericin B, nystatin, griseofulvin, miconazole, ketoconazole, tioconazole, econazole or clotrimazole.

2. The cream formulation as defined in claim 1 wherein the solubilizer for tipredane is a mixture of propylene glycol and water.

3. The cream formulation as defined in claim 1 wherein the buffer is sodium citrate, potassium citrate, tromethamine, aluminum hydroxide, an alkali metal hydroxide or mixtures thereof.

4. The cream formulation as defined in claim 1 wherein the high melting point wax is white wax.

5. The cream formulation as defined in claim 1 further including one or more emollients, one or more metal chelating agents, one or more lubricants and one or more antioxidants.

6. The cream formulation as defined in claim 5 wherein the emollient is isopropyl stearate or isopropyl palmitate, the metal chelating agent is disodium ethylene diamine tetraacetate dihydrate, dipotassium ethylene diamine tetraacetate dihydrate, the lubricant is a silicone, and the preservative is benzyl alcohol.

7. The cream formulation as defined in claim 1 wherein the emulsifier is glyceryl monostearate, cetyl alcohol, polyethylene glycol 60 sorbitan monolaurate, wool alcohols or polyethylene glycol 300 stearate.

8. The cream formulation as defined in claim 4 wherein the high melting point wax is present in an amount within the range of from about 2 to about 5% by weight.

9. The cream formulation as defined in claim 1 wherein the tipredane is present in an amount within the range of from about 0.005 to about 0.5% by weight, and the solubilizer for tipredane is propylene glycol and water with the propylene glycol present in an amount within the range of from about 5 to about 30% by weight and the water present in an amount within the range of from about 30 to about 65% by weight, all of the above % being based on the total weight of the cream formulation.

10. The cream formulation as defined in claim 1 wherein the buffer is sodium citrate or potassium citrate and is present in an amount within the range of from about 0.1 to about 1% by weight and the high melting point wax is present in an amount of within the range of from about 2 to about 5% by weight.

11. The cream formulation as defined in claim 1 wherein the emulsifier is present in an amount within the range of from about 8 to about 20 weight %.

12. The cream formulation as defined in claim 5 wherein the emollients are present in an amount within the range of from about 1 to about 5 weight %, the metal chelating agent is present in the range of from about 0.002 to about 0.008 weight %, the lubricant is present in an amount within the range of from about 0.5 to about 1.5% by weight and the preservative is present in an amount within the range of from about 0.8 to about 1.5% by weight.

13. The cream formulation as defined in claim 1 having the formula

|  | % w/w | | |
| --- | --- | --- | --- |
| tipredane micronized powder | 0.05 | to | 0.3 |
| propylene glycol | 10 | to | 20 |
| sodium citrate | 0.4 | to | 0.6 |
| disodium EDTA dihydrate | 0.002 | to | 0.008 |
| benzyl alcohol | 0.8 | to | 1.5 |
| glyceryl monostearate | 5 | to | 9 |
| cetyl alcohol | 4 | to | 6 |
| white wax | 2 | to | 5 |
| isopropyl isostearate or isopropyl palmitate | 1 | to | 5 |
| polysorbate 60 | 3 | to | 6 |
| sodium metabisulfite | 0.001 | to | 0.1 |
| silicone fluid | 0.2 | to | 2 |
| aluminum hydroxide | 0.2 | to | 0.6 |
| purified water | | | |
| antifungal agent | 5 | to | 20 |

14. The cream formulation as defined in claim 1 further including more than one antifungal agent which is amphotericin B, nystatin, griseofulvin, miconazole, ketoconazole, tioconazole, econazole or clotrimazole.

15. The cream formulation as defined in claim 14 wherein the antifungal agent is tioconazole.

16. A method of treating dermatitis which comprises administering topically an effective amount of a composition as defined in claim 1.

17. A method of treating dermatitis which comprises administering topically an effective amount of a composition as defined in claim 6.

18. A method of treating dermatitis which comprises administering topically an effective amount of a composition as defined in claim 9.

19. A method of treating dermatitis which comprises administering topically an effective amount of a composition as defined in claim 13.

20. The cream formulation a defined in claim 1 wherein the antifungal agent is present in an amount within the range from about 1 to about 25% by weight of the formulation.

* * * * *